United States Patent
Dahlgren

(10) Patent No.: US 11,560,964 B2
(45) Date of Patent: Jan. 24, 2023

(54) VALVE ACTUATION DEVICE COUPLING

(71) Applicant: ACIST Medical Systems, Inc., Eden Prairie, MN (US)

(72) Inventor: Aron David Dahlgren, Edina, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 235 days.

(21) Appl. No.: 16/999,154

(22) Filed: Aug. 21, 2020

(65) Prior Publication Data

US 2022/0057012 A1 Feb. 24, 2022

(51) Int. Cl.
*F16K 31/04* (2006.01)
*F16K 11/08* (2006.01)
*F16K 27/06* (2006.01)

(52) U.S. Cl.
CPC .......... *F16K 31/043* (2013.01); *F16K 11/08* (2013.01); *F16K 27/06* (2013.01)

(58) Field of Classification Search
CPC ..... Y10T 137/86839; Y10T 137/86863; Y10T 137/86871; Y10T 137/87153;
(Continued)

(56) References Cited

U.S. PATENT DOCUMENTS 1,298,680 A * 4/1919 Dunham .................. F16D 3/04
464/170
1,496,126 A 6/1924 Livingstone
(Continued)

FOREIGN PATENT DOCUMENTS

CA 2312632 A1 12/2001
CN 2187955 Y 1/1995
(Continued)

OTHER PUBLICATIONS

"Surface Roughness," chart of amplitude parameters, Retrieved from the Internet <URL:https://en.wikipedia.org/wiki/Surface_roughness> on Sep. 18, 2017, 8 pages.
(Continued)

*Primary Examiner* — Hailey K. Do
(74) *Attorney, Agent, or Firm* — Fredrikson & Byron, P.A.

(57) ABSTRACT

A fluid injection system includes a valve device and a valve actuation device. The valve device has a valve member and a valve member coupling. The valve member has an open position that permits fluid to pass through and a closed position that prevents fluid from passing through. The valve member coupling is configured, when actuated, to transition the valve member between the open and closed positions. The valve actuation device having a valve actuation coupling and a drive mechanism. The valve actuation coupling is coupled to the valve member coupling and drive mechanism. The valve actuation coupling is movable independent of the drive mechanism to couple the valve actuation coupling to the valve member coupling. And, the valve actuation coupling is movable with the drive mechanism to actuate the valve member coupling to transition the valve member between the open and closed positions.

16 Claims, 7 Drawing Sheets

(58) Field of Classification Search
CPC ..... Y10T 137/87161; Y10T 137/87169; Y10T 137/87217; Y10T 137/5689; Y10T 137/4807; Y10T 137/2554; F16K 31/043; F16K 31/047; F16K 31/04; F16K 31/041; F16K 31/46; F16K 31/52; F16K 31/522; F16K 5/00; F16K 5/02; F16K 5/0242; F16K 5/04; F16K 5/0442; F16K 5/06; F16K 5/0647; F16K 5/0652; F16K 11/08; F16K 11/083; F16K 11/0833; F16K 11/085; F16K 11/0853; F16K 11/087; F16K 11/0873

See application file for complete search history.

(56) References Cited

U.S. PATENT DOCUMENTS

| | | | |
|---|---|---|---|
| 1,937,122 A | 11/1933 | Leach | |
| 2,538,662 A | 1/1951 | Abbott | |
| 2,893,390 A | 7/1959 | Nita Lockhart et al. | |
| 2,985,182 A | 5/1961 | Williams | |
| 3,299,904 A | 1/1967 | Burke | |
| 3,359,910 A | 12/1967 | Latham, Jr. | |
| 3,405,545 A | 10/1968 | Walker | |
| 3,411,534 A | 11/1968 | Rose | |
| 3,802,463 A | 4/1974 | Dabney | |
| 3,808,895 A * | 5/1974 | Fitzwater | F16K 31/563 251/71 |
| 3,813,077 A | 5/1974 | Kolic | |
| 3,861,421 A | 1/1975 | Thompson | |
| 3,918,490 A | 11/1975 | Goda | |
| 3,941,128 A | 3/1976 | Baldwin | |
| 4,061,142 A | 12/1977 | Tuttle | |
| 4,096,070 A | 6/1978 | Servas | |
| 4,282,902 A | 8/1981 | Haynes | |
| 4,286,442 A * | 9/1981 | Peterson | F16D 3/04 464/83 |
| 4,332,148 A * | 6/1982 | Maki | F16D 3/10 74/595 |
| 4,396,385 A * | 8/1983 | Kelly | A61M 5/14216 604/152 |
| 4,452,592 A * | 6/1984 | Tsai | F16D 3/04 74/595 |
| 4,484,599 A | 11/1984 | Hanover et al. | |
| 4,585,442 A | 4/1986 | Mannes | |
| 4,645,489 A | 2/1987 | Krumme et al. | |
| 4,969,486 A | 11/1990 | Puzio | |
| 5,071,329 A | 12/1991 | Sano et al. | |
| 5,113,906 A | 5/1992 | Hoegner | |
| 5,117,870 A | 6/1992 | Goodale et al. | |
| 5,399,172 A | 3/1995 | Martin et al. | |
| 5,421,780 A * | 6/1995 | Vukovic | E21B 43/121 464/147 |
| 5,439,452 A | 8/1995 | McCarty | |
| 5,458,581 A | 10/1995 | Hull | |
| 5,533,708 A | 7/1996 | Atkinson et al. | |
| 5,542,832 A | 8/1996 | Sone et al. | |
| 5,573,515 A | 11/1996 | Wilson et al. | |
| 5,583,630 A | 12/1996 | Kimura et al. | |
| 5,611,458 A | 3/1997 | Ogden et al. | |
| 5,704,773 A | 1/1998 | Higashiyama | |
| 5,769,385 A | 6/1998 | Burrous et al. | |
| 5,797,889 A | 8/1998 | Steinman | |
| 5,851,201 A | 12/1998 | Ritger et al. | |
| 5,901,745 A | 5/1999 | Buchtel | |
| 6,017,332 A | 1/2000 | Urrutia | |
| 6,221,045 B1 | 4/2001 | Duchon et al. | |
| 6,517,439 B1 * | 2/2003 | Sears | F16D 3/04 464/106 |
| 6,565,535 B2 | 5/2003 | Zaias et al. | |
| 6,656,157 B1 | 12/2003 | Duchon et al. | |
| 7,617,837 B2 | 11/2009 | Wilson et al. | |
| 7,985,140 B2 | 7/2011 | Maki et al. | |
| 8,152,780 B2 | 4/2012 | Evans et al. | |
| 8,851,172 B1 | 10/2014 | Dudzinski | |
| 9,739,289 B2 * | 8/2017 | Oda | F04D 29/4213 |
| 2003/0084943 A1 * | 5/2003 | Tischler | F16K 31/041 137/624.11 |
| 2005/0255426 A1 | 11/2005 | Mariaulle et al. | |
| 2007/0161970 A1 | 7/2007 | Spohn et al. | |
| 2008/0058720 A1 | 3/2008 | Spohn et al. | |
| 2008/0103446 A1 | 5/2008 | Torrance et al. | |
| 2009/0149743 A1 | 6/2009 | Barron et al. | |
| 2010/0130958 A1 | 5/2010 | Kang et al. | |
| 2010/0280462 A1 | 11/2010 | Kommireddy et al. | |
| 2012/0065502 A1 | 3/2012 | Levy et al. | |
| 2013/0053692 A1 | 2/2013 | Barron et al. | |
| 2013/0066202 A1 | 3/2013 | Barron et al. | |
| 2013/0067416 A1 | 3/2013 | Barron et al. | |
| 2014/0107480 A1 | 4/2014 | Spohn et al. | |
| 2016/0202708 A1 | 7/2016 | Hurst | |
| 2017/0370493 A1 | 12/2017 | Sigg et al. | |
| 2018/0344142 A1 | 12/2018 | Abouzgheib | |
| 2020/0033897 A1 | 1/2020 | Jensen et al. | |

FOREIGN PATENT DOCUMENTS

| | | |
|---|---|---|
| CN | 2244409 Y | 1/1997 |
| CN | 201046277 Y | 4/2008 |
| CN | 101244299 A | 8/2008 |
| CN | 101355975 A | 1/2009 |
| CN | 101461972 A | 6/2009 |
| EP | 1055432 A2 | 11/2000 |
| EP | 1410815 A1 | 4/2004 |
| GB | 2274326 A | 7/1994 |
| JP | S602369 A | 1/1985 |
| JP | H0796033 A | 4/1995 |
| WO | 0024313 A1 | 5/2000 |
| WO | 0155626 A1 | 8/2001 |
| WO | 2005110007 A2 | 11/2005 |
| WO | 2007062315 A2 | 5/2007 |
| WO | 2011002744 A1 | 1/2011 |
| WO | 2011073969 A1 | 6/2011 |

OTHER PUBLICATIONS

Wikipedia page—https://en.wikipedia.org/wiki/Coupling (see Section 2.1.21: Oldham), "Wikipedia Coupling, Oldham Coupler," retrieved from the Internet on Oct. 23, 2020, believed to be available prior to the filing date of the instant application (Aug. 21, 2020), 2 pages.

Simulation on YouTube: https://www.youtube.com/watch?v=2ibsOu_TrZc, Oldham Coupling, May 29, 2015, 71 pages.

Off the shelf Oldham couplings: https://www.ruland.com/servo-couplings/oldham-couplings.html, "Ruland Oldham Coupling," retrieved from the Internet on Oct. 23, 2020, believed to be available prior to the filing date of the instant application (Aug. 21, 2020), 8 pages.

"Oldham's Coupling," Oct. 8, 2013, XP002804706, retrieved from the Internet: URL:https://blogpuneet.wordpress.com/2013/10/08/oldhams-coupling/comment-page-1/[retrieved on Nov. 4, 2021], 2 pgs.

International Search Report and Written Opinion dated Nov. 16, 2021 for International Application No. PCT/US2021/045860, 15 pgs.

* cited by examiner

VALVE ACTUATION DEVICE COUPLING

TECHNICAL FIELD

This disclosure generally relates to valve devices, valve actuation devices, and related systems and methods. Certain such embodiments are described herein in the context of a medical fluid injection system as one exemplary type of application.

BACKGROUND

Valves can be used to control fluid flow in a variety of contexts, including in the medical context. For example, certain medical procedures may include introducing a fluid into a patient. Various medical devices, such as a fluid injection system, can be employed to introduce fluid into a patient. Injection systems can be used in a variety of medical applications, including to introduce fluid into a patient to facilitate medical diagnostic and/or interventional procedures. In some such procedures, this fluid can assist in the collection of information, such as image data, at a region of interest within the patient. This collected information can be used, for instance, to ascertain characteristics relevant to the diagnostic procedure and/or guide the placement of one or more medical devices during the interventional procedure.

In conjunction with a particular procedure, such medical devices may selectively start and stop injecting fluid into a patient, at least in part, by opening or closing a fluid pathway leading to the patient. To do so, one or more valves can be actuated to selectively open and close the one or more fluid pathways leading to the patient.

SUMMARY

In general, various embodiments relating to valve devices, valve actuation devices, and related systems and methods are disclosed herein. In particular, disclosed herein are embodiments of a valve actuation device configured to couple to a valve device. When coupled, the valve actuation device can actuate the valve device to open and close a fluid passage at the valve device.

In certain applications, the valve device may be attached to a component that is placed in a system during setup in a manner that can cause variability in the precise location of the valve device from one set up to another. In the case of a fluid injection system, the valve device may be attached to a fluid reservoir. In setting up the fluid injection system, a portion of the fluid reservoir may be placed so as to interface with a drive ram of the fluid injection system, leaving the valve device's precise location dependent on the placement of the fluid reservoir in that particular instance. This variability in the valve device's precise location from one setup to another can result, at least in part, from unavoidable manufacturing tolerances between the valve device, valve actuation device, and/or fluid reservoir. This variability can lead to substantial misalignment between the valve device and the valve actuation device, making a suitable coupling of these components difficult. Without an ability to compensate for this variability, the substantial misalignment can result in stresses being imparted on one or more of the coupled components which may lead to connection and/or component failure.

Various valve actuation device embodiments can be useful, for instance, in facilitating alignment between the valve actuation device and the valve device so that the valve actuation device can be suitably coupled to the valve device. Embodiments disclosed herein can provide a valve actuation device that can accommodate variable locations of the valve device and, thereby, compensate for misalignment with the valve device. In particular, embodiments of a valve actuation device can include a valve actuation coupling that is movable in a manner to align the valve actuation coupling with a valve member coupling, of the valve device, to facilitate a suitable coupling between the valve actuation coupling and the valve member coupling. Notably, the ability of the valve actuation device to compensate for misalignment with the valve device can reduce stresses imparted on one or both of the valve device and valve actuation device thereby reducing the risk of connection and/or component failure and increasing the useful life of these components.

One embodiment includes a fluid injection system. The fluid injection system includes a valve device and a valve actuation device. The valve device includes a valve member and a valve member coupling. The valve member defines a fluid passage. The valve member has an open position that permits fluid to pass through the valve device via the fluid passage and a closed position that prevents fluid from passing through the valve device via the fluid passage. The valve member coupling is configured, when actuated, to transition the valve member between the open position and the closed position. The valve actuation device includes a valve actuation coupling and a drive mechanism. The valve actuation coupling is coupled to the valve member coupling and the drive mechanism. The valve actuation coupling is movable independent of the drive mechanism to couple the valve actuation coupling to the valve member coupling. And, the valve actuation coupling is movable with the drive mechanism to actuate the valve member coupling to transition the valve member between the open position and the closed position.

In a further embodiment of the fluid injection system, the valve actuation coupling is movable independent of the drive mechanism in a direction that allows the valve actuation coupling to be aligned with the valve member coupling. As one such example, the drive mechanism can be configured to rotate about a drive axis, and the valve actuation coupling can be movable independent of the drive mechanism in the direction away from the drive axis. In this example, the valve member coupling can be at a location offset from the drive axis, and the valve actuation coupling can be movable independent of the drive mechanism to the location offset from the drive axis.

Another embodiment includes a valve actuation device. The valve actuation device includes a drive mechanism and a valve actuation coupling. The drive mechanism is configured to rotate about a drive axis. The valve actuation coupling is coupled to the drive mechanism. The valve actuation coupling is movable in a direction away from the drive axis independent of the drive mechanism to couple the valve actuation coupling to a valve member coupling. And, the valve actuation coupling is movable with the drive mechanism to actuate the valve member coupling to transition a valve member between an open position and a closed position.

In a further embodiment of the valve actuation device, the valve actuation device includes a limiting plate defining an aperture through the limiting plate. The aperture has a first dimension and a second dimension that is perpendicular to the first dimension. The valve actuation coupling extends through the aperture of the limiting plate. The valve actuation coupling is movable in the direction away from the drive axis independent of the drive mechanism along the first dimension. And, the second dimension is sized to limit movement of the valve actuation coupling in the direction away from the drive axis independent of the drive mechanism along the second dimension to be less than that along the first dimension.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

FIG. 3A shows a valve member of the valve device in a closed position. FIG. 3B shows the valve member of the valve device in a first open position. FIG. 3C shows the valve member of the valve device in a second open position.

DETAILED DESCRIPTION

The following detailed description is exemplary in nature and is not intended to limit the scope, applicability, or configuration of the invention in any way. Rather, the following description provides some practical illustrations for implementing embodiments of the present invention. Examples of constructions, materials, and/or dimensions are provided for selected elements. Those skilled in the art will recognize that many of the noted examples have a variety of suitable alternatives.

Figure 1:
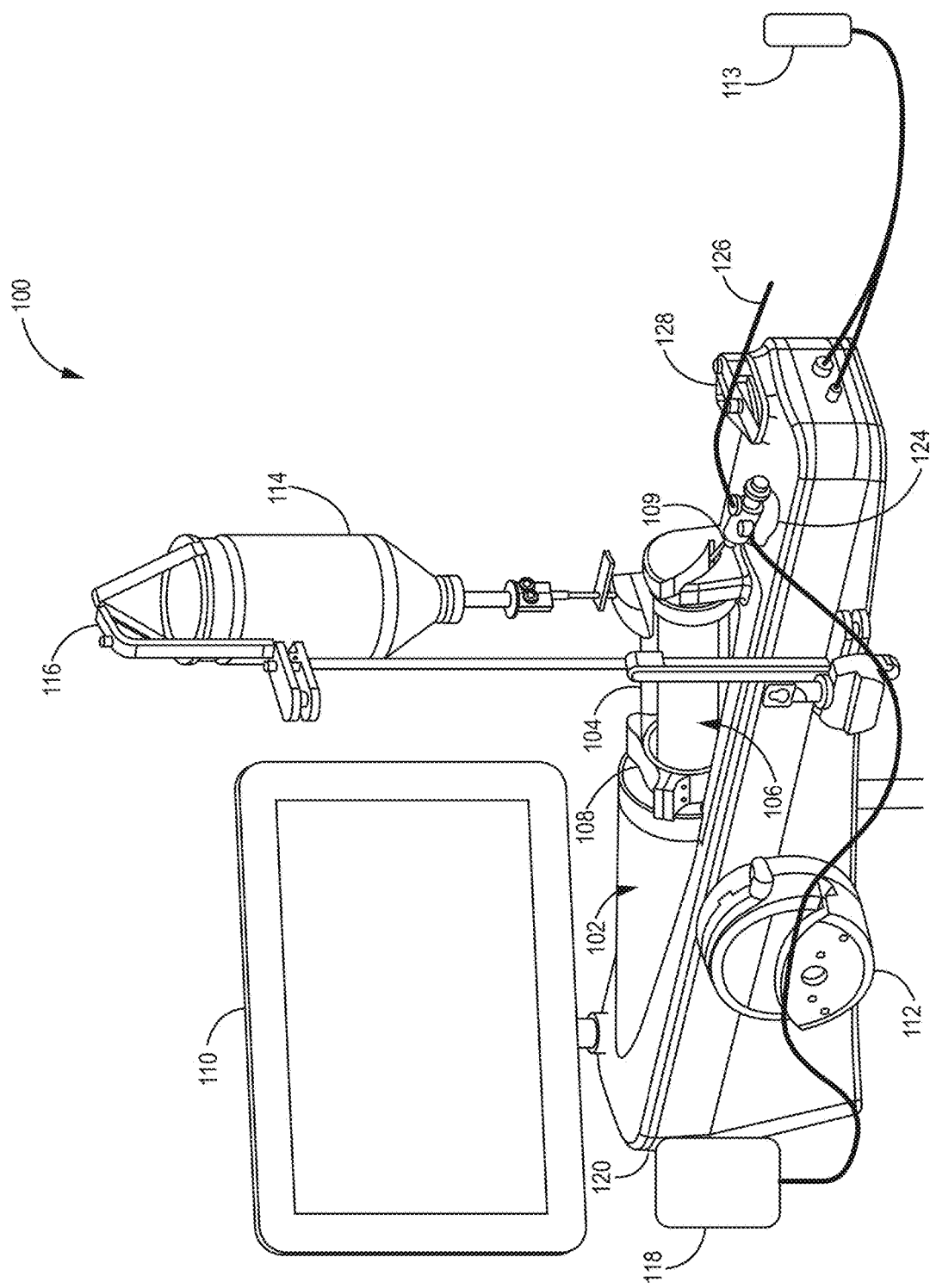
FIG. 1 is a perspective view of an embodiment of a fluid injection system.

FIG. 1 shows a perspective view of an exemplary embodiment of a fluid injection system 100. In operation, the fluid injection system 100 can inject a quantity of fluid into a patient, for instance, into a vessel of a patient via a catheter. The fluid injected by the fluid injection system 100 can be, for example, a contrast fluid, a non-contrast fluid (e.g., saline), or a combination thereof. By injecting a quantity of fluid into a patient, the fluid injection system 100 can facilitate a variety of medical diagnostic and/or interventional procedures, including the collection of image data representing an anatomical region of interest. Such procedures can include, as examples, optical coherence tomography (OCT) imaging, intravascular ultrasound (IVUS) imaging, computed tomography (CT) imaging, magnetic resonance imaging (MRI), angiographic procedures, and interventional device procedures/placements.

The illustrated fluid injection system 100 includes a drive assembly housing 102 and a sleeve 104. The sleeve 104 can be attached to the drive assembly housing 102. For example, the drive assembly housing 102 can include an opening, and the sleeve 104 can be secured to the drive assembly housing 102 at, or near, such opening. The sleeve 104 can extend out from the drive assembly housing 102 and can be configured to receive and secure thereat a fluid reservoir 106. Although the illustrated example in FIG. 1 shows one fluid reservoir 106, other fluid injection system embodiments can include two (or more) fluid reservoirs 106 and a corresponding number of sleeves 104. The fluid reservoir 106 can define an internal reservoir volume that includes a plunger 108. At least a portion of a drive assembly can be housed within the drive assembly housing 102.

The drive assembly can be configured to pressurize fluid within the internal reservoir volume. For instance, the drive assembly may couple to the plunger 108 via a drive ram, such as at the opening in the drive assembly housing 102, and the drive ram can drive the plunger 108 within the internal reservoir volume of the fluid reservoir 106. As the plunger 108 is progressively driven within the fluid reservoir 106 (e.g., in a direction toward an outlet of the fluid reservoir 106), fluid within the internal reservoir volume can be pressurized and output from the fluid reservoir 106 along a fluid line 109 leading to a catheter 126 that is inserted into a patient's blood vessel to inject the fluid into the vasculature. In certain applications of the fluid injection system 100, output fluid, such as contrast media, can be pressurized anywhere from 1000-1500 psi (e.g., 1200 psi). In embodiments that include two (or more) fluid reservoirs 106, a corresponding number of drive assemblies can be housed within the drive assembly housing 102 for pressurizing fluid within each fluid reservoir.

The illustrated embodiment of the fluid injection system 100 includes several features that can be useful in pressurizing and delivering fluid during operation. For example, the fluid injection system 100 can include a control panel 110. The control panel 110 can provide a user interface for various operational aspects. For example, the control panel 110 can be utilized by an operator to set up various parameters and/or protocols to be used for a given fluid injection procedure. The control panel 110 can also be used to initialize the fluid injection system 100 (e.g., to prepare it for a patient fluid injection), or to activate certain features or sequences of operation. In some cases, as shown here, a hand controller 113 can be coupled to the control panel 110 and used by an operator to remotely input injection-related commands to the fluid injection system 100. The control panel 110 may also provide status information, including information related to past or currently ongoing injection procedures as well as any appropriate alerts. The control panel 110 can include an processing engine having one or more processors for controlling operation of the fluid injection system 100. Such processors can also communicate with and/or control other components, such as the drive assembly, a peristaltic pump 112 (when present), and/or any sensors and detectors (e.g., air detection sensor 128 and/or hemodynamic pressure transducer) connected to the fluid injection system 100.

The fluid injection system 100 can also include one or more components useful for supplying fluid to be used in an injection procedure. In applications where two fluids are to be injected into a patient, a fluid supply container 114 and a fluid supply container 118 can be fluidly coupled to the fluid injector 100. As one example, the fluid supply container 114 can be a contrast fluid supply container, and the fluid supply container 118 can be a flushing fluid (e.g., saline) supply container. As shown here, a holder 116 can be included at the fluid injection system 100 to hold the fluid supply container 114, and a holder 120 can be included at the fluid injection system 100 to hold the fluid supply container 118. In the illustrated embodiment, fluid (e.g., contrast fluid) from the fluid supply container 114 can be supplied to the fluid reservoir 106 for use during an injection procedure. For example, fluid from the fluid supply container 114 can be drawn into the fluid reservoir 106 when the plunger 108 is being retracted (e.g., moved in a direction toward the drive assembly housing 102 and away from the outlet of the fluid reservoir 106) to create a negative pressure within the fluid reservoir 106 and thereby refill the internal reservoir volume. In the illustrated embodiment, the fluid injection system 100 includes a peristaltic pump 112 for delivering fluid from the fluid supply container 118 to the patient. Often times, the peristaltic pump 112 may be used to deliver non-contrast flushing fluid, such as saline, at a lower pressure than that at which the drive assembly delivers contrast fluid from the reservoir 106. Though, as noted, in other embodiments the fluid injector 100 can include a second fluid reservoir 106 and use a corresponding drive assembly housed within the drive assembly housing 102 to pressurize and deliver non-contrast fluid from the fluid supply container 118. In some such embodiments, a second fluid reservoir 106 and corresponding drive assembly may be present lieu of the peristaltic pump 112.

A manifold connector 124 can be included to selectively place one of the fluid reservoir 106 and peristaltic pump 112 (or second fluid reservoir 106, depending on the embodiment) in communication with the patient. Accordingly, the manifold connector 124 can selectively place fluid from the fluid supply container 114 and fluid from the fluid supply container 118 in communication with the patient. For example, in response to a change in pressure, the manifold connector 124 can switch from allowing fluid communication to the patient from one of the fluid reservoir 106, and fluid supply container 118, to the other of the peristaltic pump 112 (or second fluid reservoir 106, depending on the embodiment) and fluid supply container 118. A patient interface connector can also be included, for instance at the fluid line 109, to selectively permit fluid, such as fluid from the manifold connector 124, to pass therethrough, such as to a patient interfacing component (e.g., catheter, such as an injection catheter). The patient interface connector can include a valve that is configured to selectively permit fluid to be communicated through the patient interface connector.

As noted, one or more sensors can be connected to the fluid injection system 100 to provide information relating to an injection. In the illustrated embodiment, the air detection sensor 128 and hemodynamic pressure transducer are connected to the fluid injection system 100. The air detection sensor 128 can be configured to detect the presence of air (e.g., one or more air bubbles) in one or more components. As shown here, the air detection sensor 128 can be configured to detect the presence of air in the fluid line 109 at a location between an outlet of the manifold connector 124 and the patient. For instance, the fluid line 109 can have an air detection interface at which the air detection sensor 128 can detect the presence of air in the fluid line 109. The air detection sensor 128 can output a signal at the fluid injection system 100 when such air is detected, and the fluid injection system 100 can take a corresponding action, such as stopping an injection and/or providing a warning to a user. The hemodynamic pressure transducer can be configured to measure pressure, for instance in the fluid line 109. When the manifold connector 124 is open such that the hemodynamic pressure transducer is in fluid communication with the patient, the hemodynamic pressure transducer can output a signal corresponding to a pressure internal to a patient.

Preparing a fluid injection system for use can require a number of steps. Because some components used in a fluid injection are routinely replaced (e.g., after a single use, after a predetermined number of uses), preparing a fluid injection system for use can include frequently replacing and appropriately coupling together new components. Component coupling often should be precise in order to reduce stresses imparted on the coupled components and to prevent component failure and/or fluid leakage. Accordingly, replacing and appropriately coupling components in a fluid injection system can consume substantial time and require detailed attention. However, certain fluid injection system applications can be time-sensitive and may make it difficult in real-time to devote the attention to detail needed to properly prepare the fluid injection system for such applications. This can be particularly true where two components may not align precisely in the same manner from one fluid injection system set up to another.

The present disclosure describes embodiments that can facilitate alignment between coupled components. This can be useful in applications where the precise location of the coupling can vary one coupling to another, such as from one fluid injection system set up to another. As will be described further below, valve actuation device embodiments disclosed herein can be useful, for instance, in facilitating alignment between the valve actuation device and the valve device so that the valve actuation device can be suitably coupled to the valve device. Embodiments disclosed herein can provide a valve actuation device that can accommodate variable locations of the valve device and, thereby, compensate for misalignment with the valve device. The ability of the valve actuation device to compensate for misalignment with the valve device can reduce stresses imparted on one, or both, of the valve device and valve actuation device thereby reducing the risk of connection and/or component failure and increasing the useful life of these components.

Figure 2:
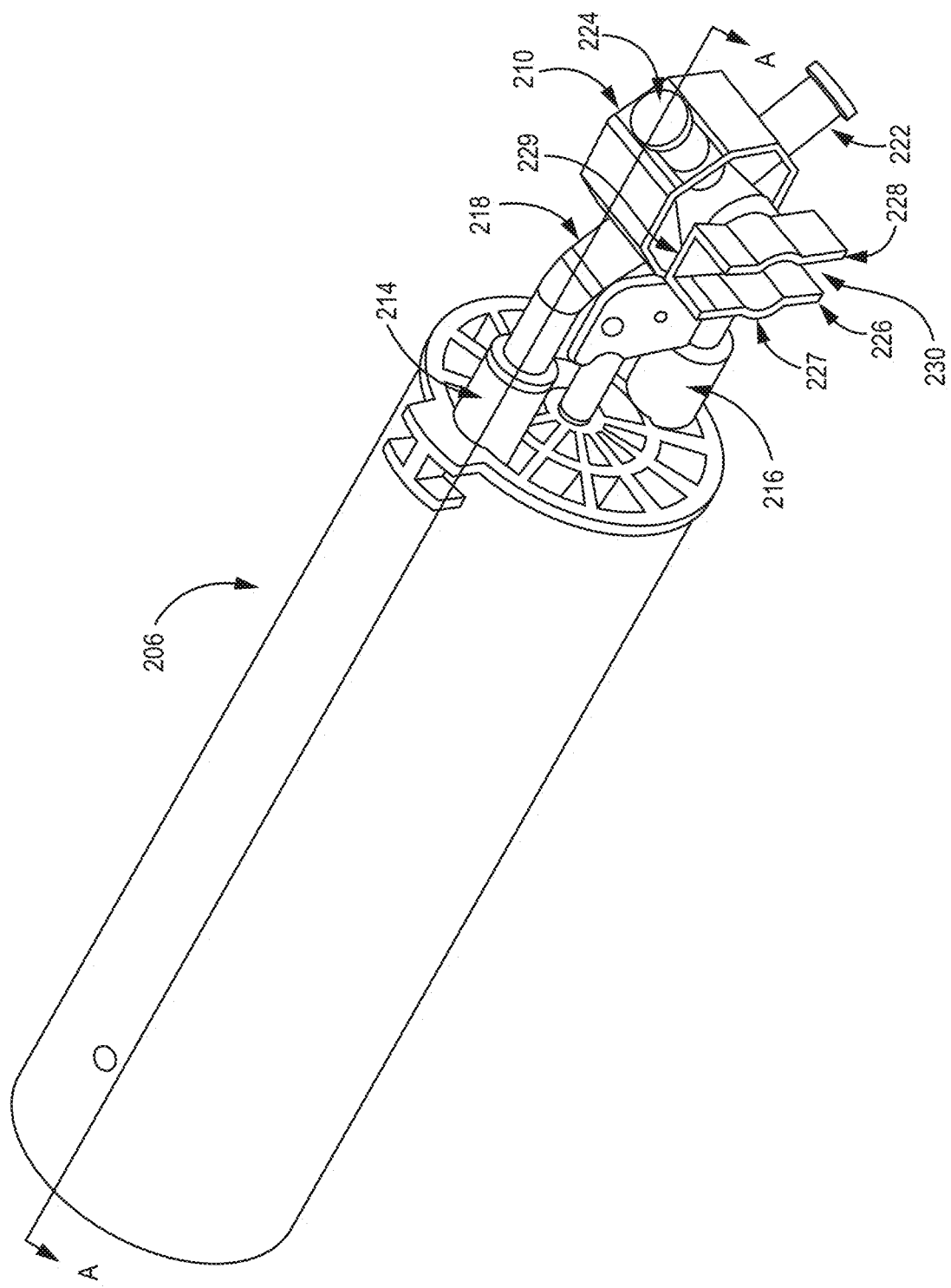
FIG. 2 is a perspective view of embodiments of a fluid reservoir and a valve device that, for instance, can be used in a fluid injection system.
Figure 3A:
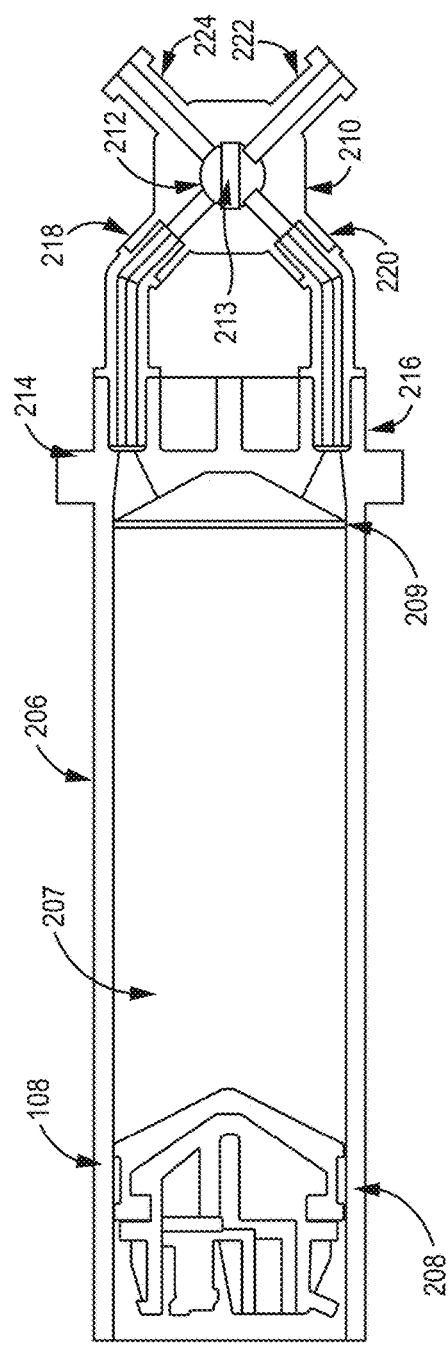
FIGS. 3A-3C show cross-sectional views of the fluid reservoir and valve device taken along line A-A in FIG. 2.
Figure 3C:
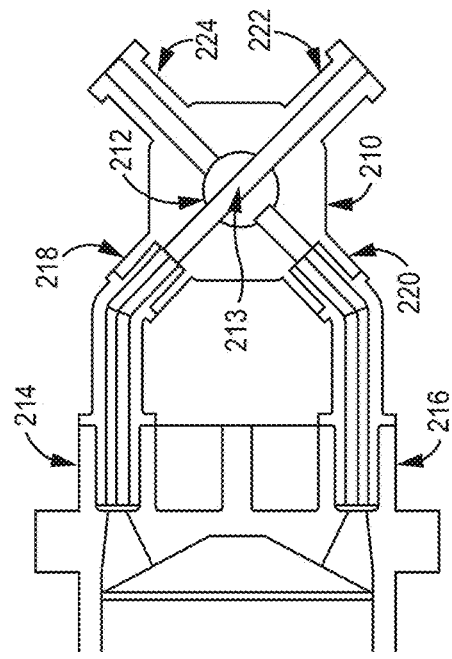
Figure 3B:
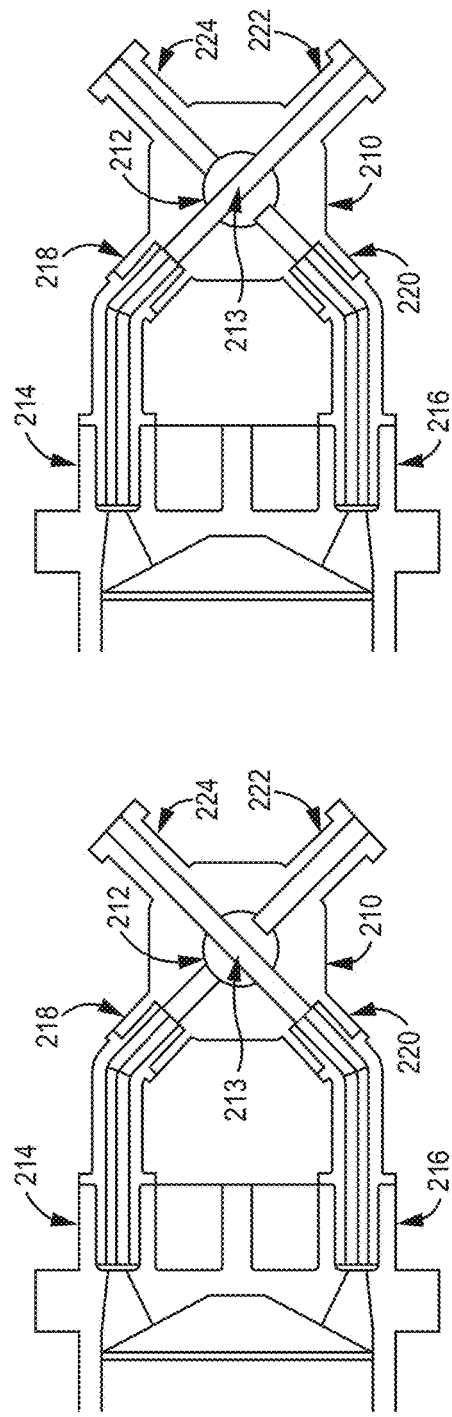

FIGS. 2 and 3A-3C show an embodiment a fluid reservoir 206 and an embodiment of a valve device 210. The fluid reservoir 206 and the valve device 210 can, for instance, be used in a fluid injection system, such as the fluid injection system 100 referenced previously. FIG. 2 shows a perspective view of the fluid reservoir 206 connected to the valve device 210. FIGS. 3A-3C show cross-sectional views of the fluid reservoir 206 and valve device 210 taken along line A-A in FIG. 2. FIG. 3A shows a valve member 212 of the valve device 210 in a closed position. FIG. 3B shows the valve member 212 of the valve device 210 in a first open position. FIG. 3C shows the valve member 212 of the valve device 210 in a second open position.

The fluid reservoir 206 defines define an internal reservoir volume 207 that includes the plunger 108. The fluid reservoir 206 can be placed at a fluid injection system such that the plunger 108 couples to the drive assembly (e.g., the drive ram) of the fluid injection system. The drive assembly can be configured to move the plunger 108 within the internal reservoir volume 207, such as between a retracted position 208 and an extended position 209. Moving the plunger 108 from the retracted position 208 to the extended position 209 can act to pressurize fluid within the internal reservoir volume 207. And, moving the plunger 108 from the extended position 209 to the retracted position 208 can act to draw fluid into the internal reservoir volume 207.

The fluid reservoir 206, as shown here, can be fluidly connected to the valve device 210. The illustrated fluid reservoir 206 includes an inlet port 214 and an outlet port 216. Each of the inlet port 214 and the outlet port 216 can be in fluid communication with the internal reservoir volume 207. The illustrated valve device 210 includes the valve member 212 as well as a first port 218, a second port 220, a third port 222, and a fourth port 224. The first port 218 can be in fluid connection with the inlet port 214 and the second port 220 can be in fluid connection with the outlet port 216.

The valve member 212 of the valve device 210 can be configured to selectively permit fluid to flow through the valve device 210 and prevent fluid from flowing through the valve device 210. The valve member 212 defines a fluid passage 213. In the illustrated embodiment, the valve member 212 can be configured to selectively permit fluid to flow through the valve device 210 and prevent fluid from flowing through the valve device 210 by selectively placing the fluid passage 213 into, and out of, fluid communication with two or more of the ports 218, 220, 222, 224.

FIG. 3A shows a closed position of the valve member 212. The closed position of the valve member 212 can prevent fluid from passing through the valve device 210 via the fluid passage 213. In the closed position, as shown in FIG. 3A, the fluid passage 213 is not in fluid communication with any of the ports 218, 220, 222, 224. Rather, in the closed position of FIG. 3A, each of the ports 218, 220, 222, 224 interfaces with a solid surface of the valve member 212 which acts to block fluid from flowing past the valve member 212. In certain applications, preventing fluid from passing through the valve device 210 via the fluid passage 213 in the closed position can mean that fluid is substantially blocked from passing through the fluid passage 213, although there could be nominal fluid leakage through the fluid passage 213 depending on certain manufacturing tolerances at the valve member 212.

FIG. 3B shows an open position of the valve member 212. The valve member 212 can be transitioned between the closed position, such as that shown in FIG. 3A, and the open position, such as that shown in FIG. 3B, by moving the valve member 212 to adjust the positioning of the fluid passage 213. The open position of the valve member 212 can permit fluid to pass through the valve device 210 via the fluid passage 213. In the open position, such as that shown in FIG. 3B, the fluid passage 213 is in fluid communication with each of the second port 220 and the fourth port 224. The open position of FIG. 3B thus permits fluid from the outlet port 216 of the fluid reservoir 206 to pass through the valve device 210 via the fluid passage 213. In this open position, fluid can flow from the outlet port 216, into the second port 220, through the fluid passage 213, and exit the valve device 210 at the fourth port 224. At the same time, the open position of FIG. 3B may prevent fluid from passing from the inlet port 214 of the fluid reservoir 206 through the valve device 210 via the fluid passage 213.

FIG. 3C shows a second open position of the valve member 212. The valve member 212 can be transitioned between the closed position, such as that shown in FIG. 3A, the first open position, such as that shown in FIG. 3B, and the second open position, such as that shown in FIG. 3C, by moving the valve member 212 to adjust the positioning of the fluid passage 213. Like the first open position shown in FIG. 3B, the second open position of the valve member 212 shown in FIG. 3C can permit fluid to pass through the valve device 210 via the fluid passage 213. In the second open position, such as that shown in FIG. 3C, the fluid passage 213 is in fluid communication with each of the first port 218 and the third port 222. The second open position of FIG. 3C thus permits fluid from the inlet port 214 of the fluid reservoir 206 to pass through the valve device 210 via the fluid passage 213. In this second open position, fluid can flow from the third port 222, through the fluid passage 213, into the first port 218 and exit the valve device 210 into the inlet port 214. At the same time, the second open position of FIG. 3C may prevent fluid from passing from the outlet port 216 of the fluid reservoir 206 through the valve device 210 via the fluid passage 213. Thus, the second open position, such as shown in FIG. 3C, can be configured to permit fluid to enter the fluid reservoir 206 via the fluid passage 213, while the first open position, such as shown in FIG. 3B, can be configured to permit fluid to exit the fluid reservoir 206 via the fluid passage 213.

The valve device 210 include a valve member coupling 226 that is configured, when actuated, to transition the valve member 212 between the open position (e.g., the first and second open positions) and the closed position. The valve member coupling 226 can be coupled to the valve member 212 such that a force applied at the valve member coupling 226 is transferred to the valve member 212 causing the valve member 212 to move between the open and closed positions. For instance, the valve member 212 can be in the closed position, such as that shown in FIG. 3A, when the fluid reservoir 206 is secured in place at the fluid injection system. Then, when the fluid reservoir 206 is to be filled with fluid, the valve member coupling 226 can be actuated to transition the valve member 212 from the closed position to an open position, such as the second open position shown in FIG. 3C, so that fluid can be drawn into the fluid reservoir 206 (e.g., by retracting the plunger 108) through the valve device 210 via the fluid passage 213. Then, when fluid is to be pressurized and output from the fluid reservoir 206, the valve member coupling 226 can be actuated to transition the valve member 212 from one open position (e.g., the fill open position shown in FIG. 3C) to another open position, such as the first open position shown in FIG. 3B, so that fluid can be output from the fluid reservoir 206 (e.g., by advancing the plunger 108 toward the outlet port 216) through the valve device 210 via the fluid passage 213. When the fluid reservoir 206 is not being used, the valve member coupling 226 can be actuated to transition the valve member 212 from the open position to the closed position, such as that shown in FIG. 3A, to prevent fluid from exiting the fluid reservoir 206.

The valve member coupling 226 can define a structure suitable for coupling to another component, such as a valve actuation coupling, receiving an actuation force from this component, and transferring the actuation force to the valve member 212. The illustrated embodiment of the valve member coupling 226 includes a first side wall 227, a second side wall 228, and a back wall 229. The second side wall 228 is opposite the first side wall 227, and the back wall 229 extends between the first side wall 227 and the second side wall 228. The first side wall 227, the second side wall 228, and the back wall 229 together can define a fitting 230. The fitting 230 can be configured to be complementary to and couple to another component. For example, the fitting 230 can be configured to be complementary to and couple to a valve actuation coupling. As such, in this example, the valve actuation coupling can be received between the first side wall 227 and the second side wall 228 of the valve member coupling 226.

Figure 4:
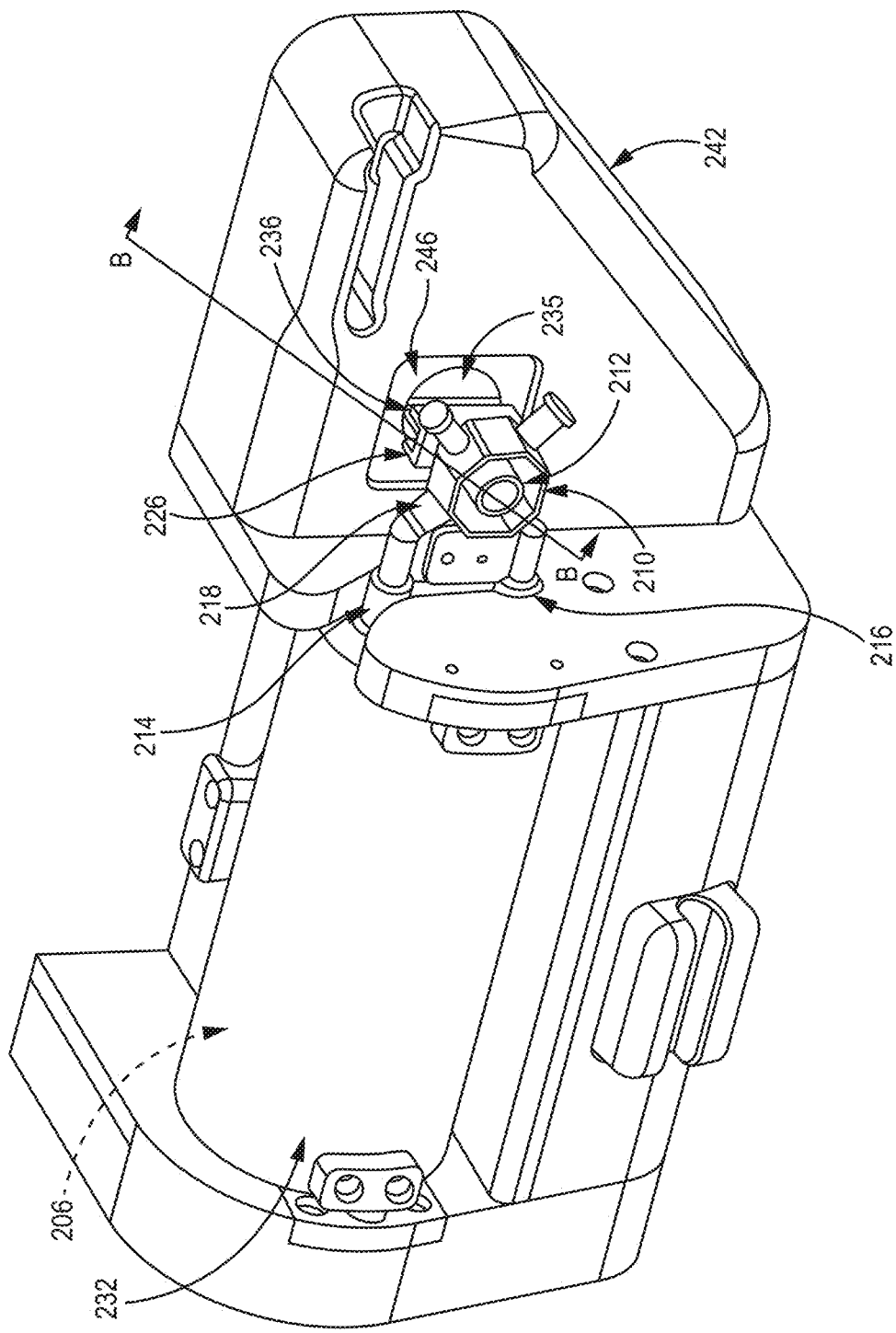
FIG. 4 is a perspective view of the fluid reservoir and valve device of FIGS. 2 and 3A-3C with the valve device coupled to an embodiment of a valve actuation device.
Figure 5:
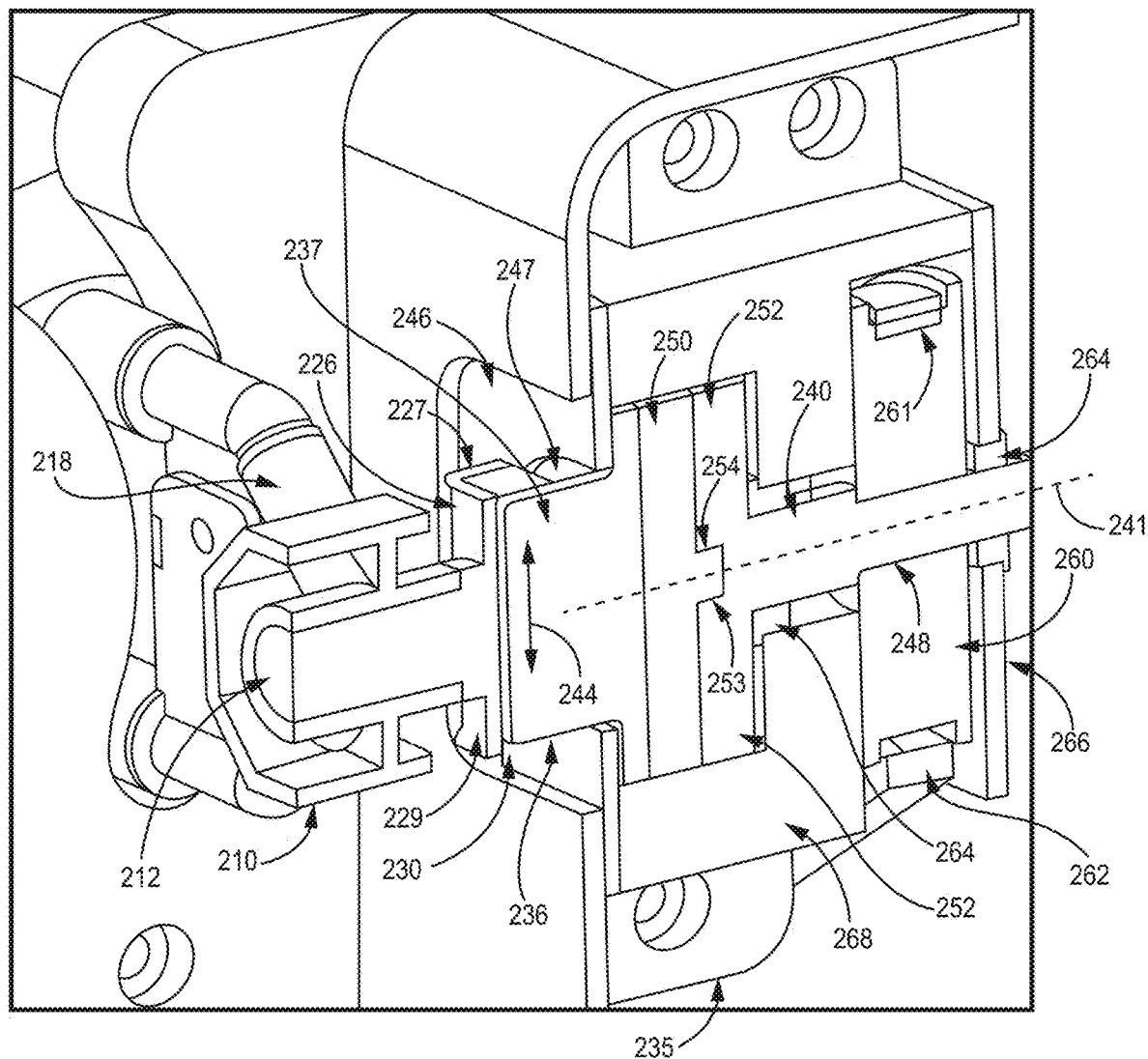
FIG. 5 is a cross-sectional view of the valve device coupled to the valve actuation device taken along line B-B in FIG. 4.

FIGS. 4 and 5 show the valve device 210 coupled to an embodiment of a valve actuation device 235. FIG. 4 shows a perspective view of the fluid reservoir 206 and valve device 210, of FIGS. 2 and 3A-3C, with the valve device 210 coupled to the valve actuation device 235. FIG. 5 is a cross-sectional view of the valve device 210 coupled to the valve actuation device 235 taken along line B-B in FIG. 4. The valve actuation device 235 can be used to actuate the valve device 210 and, thereby, transition the valve member 212 between the open position (e.g., the first and second open positions) and the closed position.

As shown in FIG. 4, the fluid reservoir 206, with the attached valve device 210, can be secured at a sleeve 232 of a fluid injection system. In particular, the fluid reservoir 206 is generally secured at the sleeve 232 in a manner that couples the plunger, within the fluid reservoir 206, to the drive ram of the fluid injection system's drive assembly. Due to manufacturing tolerances of the fluid reservoir 206 and attached valve device 210, the precise location of the valve device 210, and associated valve member coupling 226, after coupling the plunger to the drive arm can vary each time a fluid reservoir is secured at the sleeve 232. To account for such variability in the location of the valve device 210 and associated valve member coupling 226, the valve actuation device 235 can be configured to move in a direction that allows the valve actuation device 235 to couple to the valve device 210 at multiple different valve device 210 locations. Thus, the valve actuation device 235 can accommodate variable locations of the valve device 210 and, thereby, compensate for any misalignment with the valve device 210 once the fluid reservoir 206 has been secured in place.

The valve actuation device 235 can include a valve actuation coupling 236. The valve actuation coupling 236 is configured to couple to the valve device 210. In particular, the valve actuation coupling 236 can be coupled to the valve member coupling 226. As such, the valve actuation coupling 236 forms a fitting complementary to the fitting 230 formed by the valve member coupling 226. In the illustrated embodiment, the valve actuation coupling 236 includes an actuation arm 237 that is coupled to the valve member coupling 226. In particular, the actuation arm 237 can be received within the fitting 230, of the valve member coupling 226, formed between the first side wall 227 and the second side wall 228. In other embodiments, the configuration can be the inverse of that shown here such that the fitting 230, of the valve member coupling 226, can be received within the actuation arm 237 that defines a receptacle formed by two side walls and a back wall.

The valve actuation device 235 can also include a drive mechanism 240. The drive mechanism 240 can be coupled to the valve actuation coupling 236, and the drive mechanism 240 can provide a motive force to the valve actuation coupling 236 to thereby actuate the valve member coupling 226. In this way, the valve actuation coupling 236 can be movable with the drive mechanism 240 to actuate the valve member coupling 226 to transition the valve member 212 between the open position and the closed position. For example, at least a portion of the drive mechanism 240 can be configured to rotate about a drive axis 241 and, in turn, provide a rotational motive force to the valve actuation coupling 236 to thereby actuate the valve member coupling 226.

To provide the motive force to actuate the valve member coupling 226, a motive source 242 can be included in the fluid injection system. The motive source 242 can be coupled to the drive mechanism 240. As such, the motive source 242 can be configured to provide a motive force to drive (e.g., rotatably drive) the drive mechanism 240 and actuate the valve member coupling 226 to transition the valve member 212 between the open and closed positions. The motive source 242 can be in the form of a variety of suitable sources, including various types of motors having a size and motive force generation capacity suitable for inclusion in the fluid injection system.

To control the motive source 242, the fluid injection system can also include a controller. In some embodiments, the controller can be configured to control transitioning the valve member 212 between the open and closed positions by controlling the motive force that the motive source 242 provides to the drive mechanism 240. As one example, this controller can be the control panel 110 shown and described in reference to FIG. 1. The controller can include one or more processors for executing computer-readable instructions stored in a non-transitory storage medium to enable the controller to receive an input and, in response, generate and send an output command to cause the motive source 242 to turn on/off and/or adjust the amount of motive force provided to the drive mechanism 240. For instance, the controller could receive a valve open instruction as input, for instance as a result of a user inputting a valve open request at the control panel 110. And, in response, the controller could generate and send an output command to the motive source 242 to cause the motive source 242 to provide an amount of motive force to the drive mechanism 240 sufficient to transition the valve member 212 from the closed position to the open position or from one open position to another open position. In some embodiments, the controller could receive an input command in the form of data from one or more other injection system components, such as the drive assembly. And, in response to the data from one or more other injection system components being at a predetermined threshold (e.g., the drive assembly at a predetermined location or cycle), the controller could generate and send an output command to the motive source 242 to cause the motive source 242 to provide an amount of motive force to the drive mechanism 240 sufficient to transition the valve member 212 from the closed position to the open position or from one open position to another open position.

Notably, as referenced previously, to accommodate variable locations of the valve device 210 and associated valve member coupling 226, the valve actuation device 235 can be configured to move as needed to couple to the valve device 210 at multiple different valve device 210 locations. In the illustrated embodiment, the valve actuation coupling 236 of the valve actuation device 235 is movable independent of the drive mechanism 240, and relative to the valve member coupling 226, to couple the valve actuation coupling 236 to valve member coupling 226. Thus, the valve actuation coupling 236 is both movable independent of the drive mechanism 240 to couple to valve member coupling 226 and movable with the drive mechanism 240 to actuate the valve member coupling 226 to transition the valve member 212 between the open and closed positions.

More particularly, in the illustrated embodiment, the valve actuation coupling 236 is movable independent of the drive mechanism 240 in a direction that allows the valve actuation coupling 236 to be aligned with the valve member coupling 226. In many fluid injection system applications, misalignment between the valve member coupling 226 and the valve actuation coupling 236 can occur along a direction 244 shown in FIG. 5. As such, in the example described here, the valve actuation coupling 236 is movable independent of the drive mechanism 240 in the direction 244 so as to better align the valve member coupling 226 and the valve actuation coupling 236 along the direction 244. In the illustrated embodiment, the valve actuation coupling 236 is movable independent of the drive mechanism 240 in the direction 244 which is away from the drive axis 241. As such, the valve member coupling 226 can be at a location that is offset from the drive axis 241, and the valve actuation coupling 236 can be movable independent of the drive mechanism 240 to that location offset from the drive axis 241. Such movement of the valve actuation coupling 236 can be relative to the valve member coupling 226. Specifically, as shown, for instance in FIG. 5, the valve actuation coupling 236 can be movable independent of the drive mechanism 240 relative to the first side wall 227 and the second side wall 228. This movement of the valve actuation coupling 236 can result in a positioning a greater surface area of the actuation arm 237 within the fitting 230 defined by the valve member coupling 226.

In some embodiments, it may be useful to constrain movement of the valve actuation coupling 236 in one or more directions. Namely, it may be useful to constrain movement of the valve actuation coupling 236 in one or more directions other than the direction (e.g., the direction 244) that the valve actuation coupling 236 is movable independent of the drive mechanism 240 to better align the valve member coupling 226 and the valve actuation coupling 236.

To constrain movement of the valve actuation coupling 236 in or more directions, the illustrated embodiment of the valve actuation device 235 includes a limiting plate 246. The limiting plate 246 can define an aperture 247 extending through the limiting plate 246. As shown in FIG. 5, the valve actuation coupling 236 can extend through the aperture 247 of the limiting plate 246. The aperture 247 can have a first dimension and a second dimension that is perpendicular to the first dimension. In the illustrated embodiment, the first dimension extends parallel to the direction 244 and the second dimension extends perpendicular to the direction 244. As such, the valve actuation coupling 236 can be movable, independent of the drive mechanism 240, along the first dimension. The second dimension can be sized to limit movement of the valve actuation coupling 236, independent of the drive mechanism 240, along the second dimension to be less than that along the first dimension. In one example, the second dimension can be sized to substantially prohibit movement of the valve actuation coupling 236, independent of the drive mechanism 240, along the second dimension. Thus, this embodiment of the limiting plate 246 can be configured to permit movement of the valve actuation coupling 236, independent of the drive mechanism 240, in a direction (e.g., the direction 244) to align with, and couple to, the valve member coupling 226 but constrain the valve actuation coupling 236 to have less movement in one or more other directions. Conversely, in another embodiment, such as where the valve actuation coupling 236 can be movable, independent of the drive mechanism 240, along the second dimension, the first dimension can be sized to limit movement of the valve actuation coupling 236, independent of the drive mechanism 240, along the first dimension to be less than that along the second dimension. In such example, the first dimension can be sized to substantially prohibit movement of the valve actuation coupling 236, independent of the drive mechanism 240, along the first dimension. Thus, this alternate embodiment of the limiting plate 246 can be configured to permit movement of the valve actuation coupling 236, independent of the drive mechanism 240, in a direction (e.g., perpendicular to the direction 244) to align with, and couple to, the valve member coupling 226 but constrain the valve actuation coupling 236 to have less movement in one or more other directions.

Figure 6:
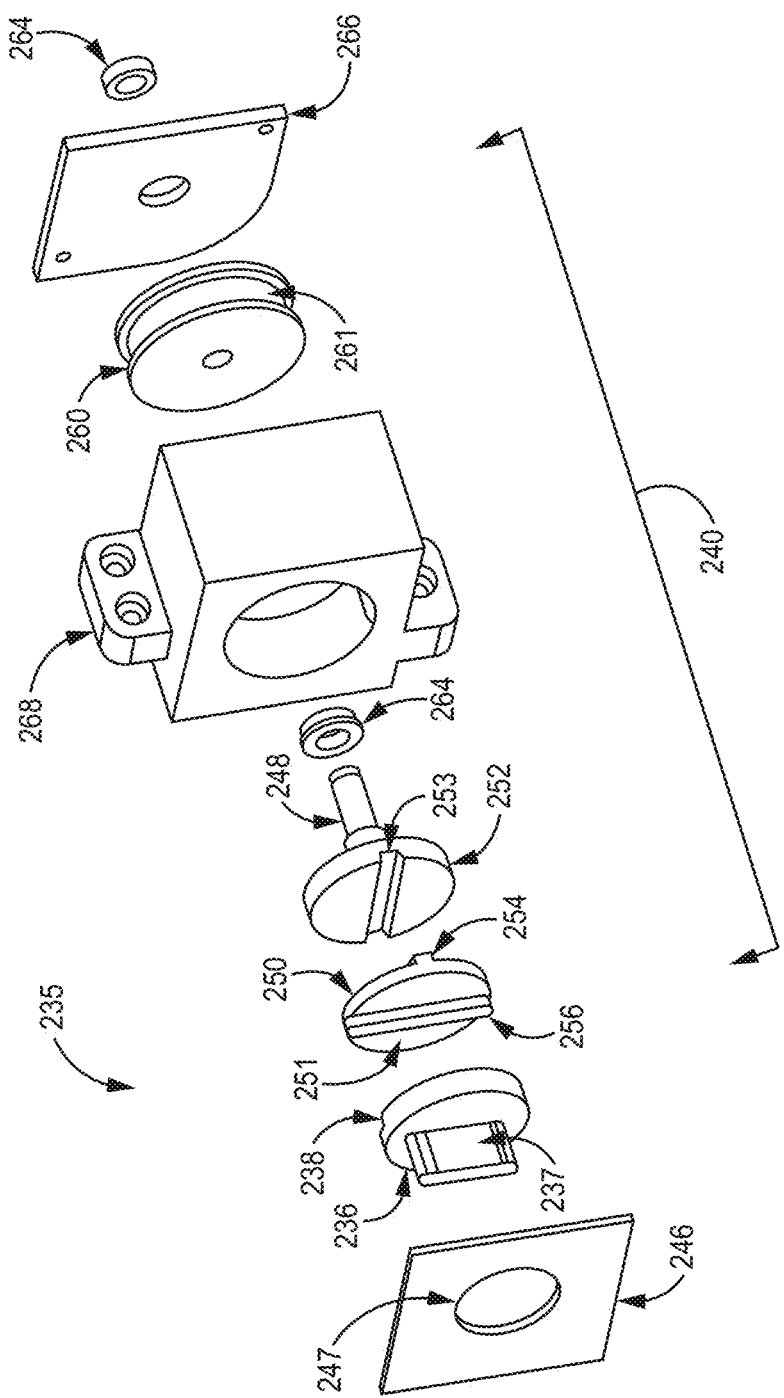
FIG. 6 is an exploded perspective view of the valve actuation device of FIGS. 4 and 5.

FIG. 6 shows an exploded perspective view of the valve actuation device 235. As noted, the valve actuation device 235 can include the valve actuation coupling 236 and the drive mechanism 240. Components making up the valve actuation device 235 and the drive mechanism 240 can allow the valve actuation coupling 236 to be both movable independent of the drive mechanism 240, to couple to the valve member coupling, and movable with the drive mechanism 240, to actuate the valve member coupling 226.

The drive mechanism 240 can include a drive shaft 248 and a transfer connector 250. The drive shaft 248 includes a drive shaft coupling 252. In the illustrated embodiment, the drive shaft coupling 252 includes a first slot 253 defined at an end portion of the drive shaft 248. The transfer connector 250 includes a first transfer coupling 254 and a second transfer coupling 256. In the illustrated embodiment, the first transfer coupling 254 includes a first extended flange extending out from a base 251 of the transfer connector 250, and the second transfer coupling 256 includes a second extended flange extending out from an opposite side of the base 251 of the transfer connector 250.

As shown, the drive shaft 248 can couple to the valve actuation coupling 236 via the transfer connector 250. The transfer connector 250 is positioned between the drive shaft 248 and the valve actuation coupling 236. In particular, the drive shaft coupling 252 can be complementary to and coupled to the first transfer coupling 254, and the valve actuation coupling 236 can be complementary to and coupled to the second transfer coupling 256. The valve actuation coupling 236 can include a second slot 238 defined at an end portion of the valve actuation coupling 236. The second slot 238 can be at an end portion of the valve actuation coupling 236 that is opposite an end portion of the valve actuation coupling 236 from which the actuation arm 237 extends out. The second extended flange of the second transfer coupling 256 can be received at the second slot 238, and the first extended flange of the first transfer coupling 254 can be received at the first slot 253.

In the illustrated embodiment, the transfer connector 250 can enable the valve actuation coupling 236 to be both movable independent of the drive mechanism 240 and movable with the drive mechanism 240. Specifically, the illustrated example can be configured such that, in operation, the drive shaft 248 can rotate about the drive axis 241 and rotatably drive the transfer connector 250 via the first slot 253 and first extended flange of the first transfer coupling 254. The transfer connector 250 can transfer this rotational drive force to the valve actuation coupling 236 via the second slot 238 and second extended flange of the second transfer coupling 256. This can enable the valve actuation coupling 236 to be movable (e.g., rotatably) with the drive mechanism 240 to actuate the valve member coupling 226 to transition the valve member 212 between open and closed positions. At the same time, the illustrated example can be configured such that, in operation, the valve actuation coupling 236 can move relative to the transfer connector 250. In particular, the valve actuation coupling 236 can be movable relative to the second transfer coupling 256 via the second slot 238 and the second extended flange of the second transfer coupling 256. This can enable the valve actuation coupling 236 to be movable (e.g., in a direction perpendicular to the drive axis, such as the direction 244) independent of the drive mechanism 240 to couple the valve actuation coupling 236 to valve member coupling 226.

As one example, the valve actuation device 235 can include an Oldham coupling. The Oldham coupling can be used to couple the valve actuation coupling 236 to the drive mechanism 240. In particular, the Oldham coupling can be configured to enable the valve actuation coupling 236 to be both movable independent of the drive mechanism 240, to couple the valve actuation coupling 236 to the valve member coupling 226, and movable with the drive mechanism 240, to actuate the valve member coupling 226 to transition the valve member 212 between open and closed positions. In such an example, the Oldham coupling can be formed by the transfer connector 250 as well as the drive shaft coupling 252 and surface of the valve actuation coupling 236 interfacing with the transfer connector 250. The Oldham coupling can thus be configured to allow the drive mechanism 240 to drive the valve actuation coupling 236 and to also allow the valve actuation coupling 236 to move independent of the drive mechanism (e.g., independent of the drive shaft 248, such as in a direction (e.g., the direction 244) perpendicular to the drive axis 241).

In the illustrated embodiment, the drive mechanism 240 additionally includes a rotatable wheel 260 and a linkage member 262. The linkage member 262 can be coupled to the rotatable wheel 260, for instance at a receptacle 261 defined at the rotatable wheel 260. The rotatable wheel 260 can be coupled to the drive shaft 248, for instance at an end portion of the drive shaft 248 opposite the end portion of the drive shaft 248 having the drive shaft coupling 252. The rotatable wheel 260 and the linkage member 262 can be configured to impart a motive force on the drive shaft 248 to drive the drive shaft 248 and, thereby, move the drive mechanism 240 to actuate the valve member coupling 226. In particular, the linkage member 262 can be coupled to the motive source 242 and receive motive force from the motive source 242. The linkage member 262 can transfer this motive force to the rotatable wheel 260. In this way, the linkage member 262 can be configured to rotatably drive the rotatable wheel 260 to move the drive mechanism 240 to actuate the valve member coupling 226. Other embodiments could implement varying mechanisms to impart a motive force on the drive shaft 248 to drive the drive shaft 248 and, thereby, move the drive mechanism 240 to actuate the valve member coupling 226.

In some embodiments, one or more components can be included to facilitate the described operation of the valve actuation device 235. For example, the valve actuation device 235 can include one or more bearings 264, for instance included at one or more location where relative rotation between components can take place. In the illustrated embodiment, one bearing 264 is included between the drive shaft 248 and an end plate 266. This bearing 264 can be at an end portion of the drive shaft 248, such as at an end portion of the drive shaft 248 interfacing with the rotatable wheel 260, and this bearing 264 can act to secure the rotatable drive shaft 248 to the end plate 266. In the illustrated embodiment, another bearing 264 is included between the drive shaft 248 and a mounting block 268. This bearing 264 can be at a portion of the drive shaft 248 so as to interface with the drive shaft coupling 252, and this bearing 264 can act to secure the rotatable drive shaft 248 to the mounting block 268. The end plate 266 and/or the mounting block 268 can, at least in part, form a housing of the valve actuation device 235 within which one or more components of the valve actuation device 235 can be located. The end plate 266 and/or the mounting block 268 can also provide one or more surfaces for securing certain components of the valve actuation device 235.

Figure 7:
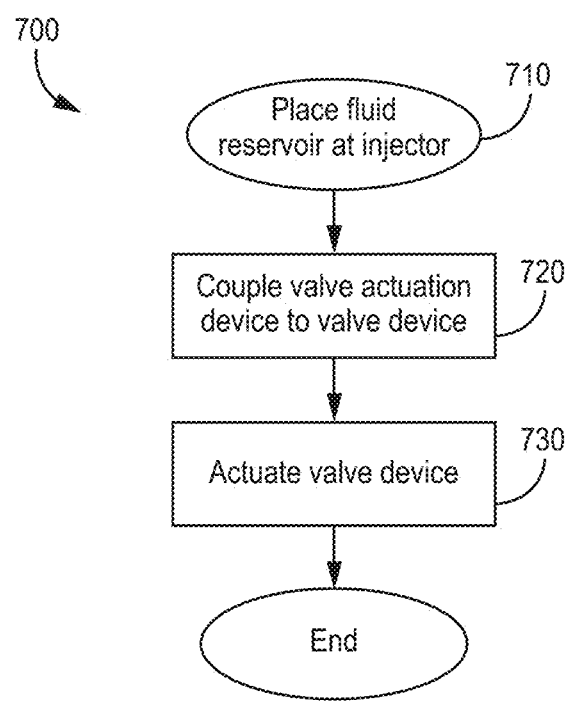
FIG. 7 is a flow diagram of an embodiment of a method of coupling a valve actuation device to a valve device and actuating the valve device.

FIG. 7 shows a flow diagram of an embodiment of a method 700 of coupling a valve actuation device to a valve device and actuating the valve device. The valve actuation device referenced in the method 700 can have one or more (e.g., all) features as disclosed herein with respect to the valve actuation device 235. The valve device referenced in the method 700 can have one or more (e.g., all) features as disclosed herein with respect to the valve device 210.

At step 710, the method 700 includes placing a fluid reservoir at a fluid injection system. The fluid reservoir referenced in the method 700 can have one or more (e.g., all) features as disclosed herein with respect to the fluid reservoir 206. For example, the fluid reservoir can be placed at the fluid injection system such that a plunger (e.g., the plunger 108) is coupled to a drive ram of the fluid injection system's drive assembly. This can include the fluid reservoir being placed at a sleeve (e.g., the sleeve 232) of the fluid injection system. Placing the fluid reservoir at the fluid injection system can result in a valve device (e.g., the valve device 210), connected to the fluid reservoir, being positioned at a location that can be a function of the placement of the fluid reservoir at the fluid injection system. Depending on the embodiment of the fluid injection system, in some cases placing the fluid reservoir at the fluid injection system can include placing the fluid reservoir in the fluid injection system, such as in the sleeve of the fluid injection system.

At step 720, the method 700 includes coupling a valve actuation device (e.g., the valve actuation device 235) to the valve device (e.g., the valve device 210 connected to the fluid reservoir). For example, the valve actuation device can include a valve actuation coupling that is coupled to a drive mechanism of the valve actuation device. In such example, coupling the valve actuation device to the valve device can include coupling the valve actuation coupling, of the valve actuation device, to a valve member coupling, of the valve device. In some instances, as a result of the fluid reservoir's placement at the fluid injection system, the valve device may not initially be aligned with the valve actuation coupling. As such, step 720 can include moving the valve actuation coupling, independent of the drive mechanism of the valve actuation device, in a direction that brings the valve actuation coupling into alignment with the valve member coupling so that the valve actuation coupling can be coupled to the valve member coupling. For instance, the drive mechanism of the valve actuation device can be configured to rotate about a drive axis and moving the valve actuation coupling can include moving the valve actuation coupling, independent of the drive mechanism of the valve actuation device, in a direction away from the drive axis (e.g., in a direction perpendicular to, and away from, the drive axis).

At step 730, the method 700 includes actuating the valve device. For example, actuating the valve device can include moving the valve actuation coupling with the drive mechanism, of the valve actuation device, to actuate the valve member coupling, of the valve device, to transition a valve member (e.g., the valve member 212), of the valve device, between open and closed positions. For instance, the valve device can be actuated as such to transition the valve member from a closed position to an open position prior to advancing a plunger within the fluid reservoir to pressurize fluid within the fluid reservoir. The valve device can also be actuated to transition the valve member from one open position (e.g., for fluid output/delivery) to another open position (e.g., for fluid filling into the fluid reservoir).

Various non-limiting exemplary embodiments have been described. It will be appreciated that suitable alternatives are possible without departing from the scope of the examples described herein. These and other examples are within the scope of the following claims.

What is claimed is:

1. A fluid injection system comprising:
   a valve device including a valve member and a valve member coupling, the valve member defining a fluid passage, the valve member having an open position that permits fluid to pass through the valve device via the fluid passage and a closed position that prevents fluid from passing through the valve device via the fluid passage, the valve member coupling configured, when actuated, to transition the valve member between the open position and the closed position; and
   a valve actuation device including a valve actuation coupling and a drive mechanism, the drive mechanism configured to rotate about a drive axis, the valve actuation coupling coupled to the valve member coupling and the drive mechanism, wherein the valve actuation coupling is movable independent of the drive mechanism in a direction away from the drive axis to a location of the valve member coupling that is offset from the drive axis to allow the valve actuation coupling to be aligned with the valve member coupling to couple the valve actuation coupling to the valve member coupling, and wherein the valve actuation coupling is movable with the drive mechanism to actuate the valve member coupling to transition the valve member between the open position and the closed position.

2. The fluid injection system of claim 1, further comprising:
   a motive source coupled to the drive mechanism, the motive source configured to provide a motive force to drive the drive mechanism and actuate the valve member coupling; and
   a controller configured to control transitioning the valve member between the open position and the closed position by controlling the motive force that the motive source provides to the drive mechanism.

3. The fluid injection system of claim 1, wherein the valve actuation device includes a limiting plate defining an aperture through the limiting plate, the aperture having a first dimension and a second dimension that is perpendicular to the first dimension, the valve actuation coupling extending through the aperture of the limiting plate, wherein the valve actuation coupling is movable independent of the drive mechanism along the first dimension, and wherein the second dimension is sized to limit movement of the valve actuation coupling independent of the drive mechanism along the second dimension to be less than that along the first dimension.

4. The fluid injection system of claim 3, wherein the second dimension is sized to prohibit movement of the valve actuation coupling independent of the drive mechanism along the second dimension.

5. The fluid injection system of claim 1, wherein the valve member coupling includes a first side wall, a second side wall opposite the first side wall, and a back wall extending between the first side wall and the second side wall, and wherein the valve actuation coupling is received between the first side wall and the second side wall of the valve member coupling.

6. The fluid injection system of claim 5, wherein the valve actuation coupling is movable independent of the drive mechanism relative to the first side wall and the second side wall.

7. The fluid injection system of claim 1, wherein the drive mechanism comprises a drive shaft and a transfer connector, the transfer connector being positioned between the drive shaft and the valve actuation coupling, the drive shaft including a drive shaft coupling and the transfer connector including a first transfer coupling and a second transfer coupling, wherein the drive shaft coupling is complementary to and coupled to the first transfer coupling, and wherein the valve actuation coupling is complementary to and coupled to the second transfer coupling.

8. The fluid injection system of claim 7, wherein the valve actuation coupling is movable relative to the second transfer coupling.

9. The fluid injection system of claim 7, wherein the drive mechanism further comprises a rotatable wheel and a linkage member, wherein the linkage member is coupled to the rotatable wheel and the rotatable wheel is coupled to the drive shaft, and wherein the linkage member is configured to rotatably drive the rotatable wheel to move the drive mechanism to actuate the valve member coupling.

10. The fluid injection system of claim 7, wherein the drive shaft coupling includes a first slot defined at an end portion of the drive shaft, the valve actuation coupling includes a second slot defined at an end portion of the valve actuation coupling, the first transfer coupling includes a first extended flange received at the first slot, and the second transfer coupling includes a second extended flange received at the second slot.

11. The fluid injection system of claim 10, wherein the valve actuation coupling includes an actuation arm extending out from the valve actuation coupling opposite the second slot, and wherein the actuation arm is coupled to the valve member coupling.

12. A fluid injection system comprising:
    a valve device including a valve member and a valve member coupling, the valve member defining a fluid passage, the valve member having an open position that permits fluid to pass through the valve device via the fluid passage and a closed position that prevents fluid from passing through the valve device via the fluid passage, the valve member coupling configured, when actuated, to transition the valve member between the open position and the closed position; and
    a valve actuation device including a valve actuation coupling and a drive mechanism, the valve actuation coupling coupled to the valve member coupling and the drive mechanism, wherein the valve actuation coupling is movable independent of the drive mechanism to couple the valve actuation coupling to the valve member coupling, and
    a fluid reservoir including an inlet port and an outlet port, wherein the valve device includes a first port and a second port, the first port in fluid connection with the inlet port and the second port in fluid connection with the outlet port, and wherein the open position of the valve member includes a first open position that permits fluid from the outlet port to pass through the valve device via the fluid passage and a second open position that permits fluid to pass through the valve device via the fluid passage and to the inlet port.

13. A valve actuation device comprising:
    a drive mechanism configured to rotate about a drive axis; and
    a valve actuation coupling coupled to the drive mechanism, wherein the valve actuation coupling is movable in a direction away from the drive axis independent of the drive mechanism to couple the valve actuation coupling to a valve member coupling, wherein the valve actuation device includes a limiting plate defining an aperture through the limiting plate, the aperture having a first dimension and a second dimension that is perpendicular to the first dimension, the valve actuation coupling extending through the aperture of the limiting plate, wherein the valve actuation coupling is movable in the direction away from the drive axis independent of the drive mechanism along the first dimension, and wherein the second dimension is sized to limit movement of the valve actuation coupling in the direction away from the drive axis independent of the drive mechanism along the second dimension to be less than that along the first dimension, and wherein the valve actuation coupling is movable with the drive mechanism to actuate the valve member coupling to transition a valve member between an open position and a closed position.

14. The valve actuation device of claim 13, wherein the drive mechanism comprises a drive shaft and a transfer connector, the transfer connector being positioned between the drive shaft and the valve actuation coupling, the drive shaft including a drive shaft coupling and the transfer connector including a first transfer coupling and a second transfer coupling, wherein the drive shaft coupling is complementary to and coupled to the first transfer coupling, and wherein the valve actuation coupling is complementary to and coupled to the second transfer coupling.

15. The valve actuation device of claim 14, wherein the valve actuation coupling is movable in the direction away from the drive axis relative to the second transfer coupling.

16. The valve actuation device of claim 14,
wherein the drive shaft coupling includes a first slot defined at an end portion of the drive shaft, the valve actuation coupling includes a second slot defined at an end portion of the valve actuation coupling, the first transfer coupling includes a first extended flange received at the first slot, and the second transfer coupling includes a second extended flange received at the second slot, and
wherein the valve actuation coupling includes an actuation arm extending out from the valve actuation coupling opposite the second slot, and wherein the actuation arm includes a cross-sectional shape configured to couple to the valve member coupling.

* * * * *